United States Patent
Kim

(10) Patent No.: US 9,008,755 B2
(45) Date of Patent: Apr. 14, 2015

(54) MEDICAL IMAGING MARKER AND PROGRAM FOR UTILIZING SAME

(75) Inventor: Han-Joon Kim, Kobe (JP)

(73) Assignee: Imagnosis Inc., Hyogo (JP)

( * ) Notice: Subject to any disclaimer, the term of this patent is extended or adjusted under 35 U.S.C. 154(b) by 515 days.

(21) Appl. No.: 12/808,673

(22) PCT Filed: Dec. 17, 2008

(86) PCT No.: PCT/JP2008/072944
§ 371 (c)(1),
(2), (4) Date: Jun. 16, 2010

(87) PCT Pub. No.: WO2009/078424
PCT Pub. Date: Jun. 25, 2009

(65) Prior Publication Data
US 2010/0268071 A1    Oct. 21, 2010

(30) Foreign Application Priority Data
Dec. 17, 2007 (JP) ................... 2007-324975

(51) Int. Cl.
| | |
|---|---|
| *A61B 5/05* | (2006.01) |
| *A61C 19/04* | (2006.01) |
| *A61B 19/00* | (2006.01) |
| *A61C 9/00* | (2006.01) |

(52) U.S. Cl.
CPC ................ *A61C 19/04* (2013.01); *A61B 19/54* (2013.01); *A61C 9/0053* (2013.01); *A61B 2019/5483* (2013.01)

(58) Field of Classification Search
None
See application file for complete search history.

(56) References Cited

U.S. PATENT DOCUMENTS

| | | | | |
|---|---|---|---|---|
| 3,983,628 | A | * | 10/1976 | Acevedo .......................... 433/24 |
| 4,425,037 | A | * | 1/1984 | Hershel et al. .................. 355/43 |
| 4,444,492 | A | * | 4/1984 | Lee .................. 355/55 |
| 5,211,164 | A | * | 5/1993 | Allen ............................ 600/426 |
| 5,224,049 | A | * | 6/1993 | Mushabac ..................... 700/163 |
| 5,237,998 | A | * | 8/1993 | Duret et al. ................... 600/476 |
| 5,257,184 | A | * | 10/1993 | Mushabac ........................ 433/75 |
| 5,343,391 | A | * | 8/1994 | Mushabac ........................ 433/76 |
| 5,347,454 | A | * | 9/1994 | Mushabac ..................... 433/214 |
| 5,359,511 | A | * | 10/1994 | Schroeder et al. .............. 433/75 |

(Continued)

FOREIGN PATENT DOCUMENTS

| | | |
|---|---|---|
| EP | 1808129 A1 | 7/2007 |
| JP | 2003-245289 A | 9/2003 |

(Continued)

*Primary Examiner* — Nicholas Evoy
(74) *Attorney, Agent, or Firm* — Rabin & Berdo, P.C.

(57) ABSTRACT

An inventive medical imaging marker includes a base (2) composed of a non-imageable material, three spherical members (10, 11, 12) provided in a predetermined positional relationship in the base (2) and each composed of an imageable material, and auxiliary marker members (20, 21, 22) provided in the base (2) and composed of the imageable material. The auxiliary marker members (20, 21, 22) respectively have linear portions (20L, 21L, 22L) which are disposed parallel to straight lines extending through center points of the three spherical members (10, 11, 12) and each have a predetermined length sufficient to serve as a mark. The center points of the three spherical members (10, 11, 12) can be correctly identified in a captured image with reference to the linear portions (20L, 21L, 22L) of the auxiliary marker members (20, 21, 22) of the inventive medical imaging marker. Thus, reference axes can be correctly defined in the image.

15 Claims, 11 Drawing Sheets

(56) References Cited

U.S. PATENT DOCUMENTS

| | | | | |
|---|---|---|---|---|
| 5,527,182 A * | 6/1996 | Willoughby | | 433/172 |
| 5,545,039 A * | 8/1996 | Mushabac | | 433/215 |
| 5,549,616 A * | 8/1996 | Schulte et al. | | 606/130 |
| 5,562,448 A * | 10/1996 | Mushabac | | 433/215 |
| 5,569,578 A * | 10/1996 | Mushabac | | 433/215 |
| 5,725,376 A * | 3/1998 | Poirier | | 433/172 |
| 5,857,853 A * | 1/1999 | van Nifterick et al. | | 433/213 |
| 5,873,721 A * | 2/1999 | Willoughby | | 433/173 |
| 5,951,475 A * | 9/1999 | Gueziec et al. | | 600/425 |
| 6,059,718 A * | 5/2000 | Taniguchi et al. | | 600/117 |
| 6,096,048 A * | 8/2000 | Howard et al. | | 606/130 |
| 6,120,290 A * | 9/2000 | Fukushima et al. | | 433/69 |
| 6,165,181 A * | 12/2000 | Heilbrun et al. | | 606/130 |
| 6,287,119 B1 * | 9/2001 | van Nifterick et al. | | 433/213 |
| 6,322,359 B1 * | 11/2001 | Jordan et al. | | 433/73 |
| 6,382,975 B1 * | 5/2002 | Poirier | | 433/173 |
| 6,402,707 B1 * | 6/2002 | Ernst | | 600/590 |
| 6,529,765 B1 * | 3/2003 | Franck et al. | | 600/427 |
| 6,546,277 B1 * | 4/2003 | Franck et al. | | 600/426 |
| 6,621,491 B1 * | 9/2003 | Baumrind et al. | | 345/419 |
| 6,662,036 B2 * | 12/2003 | Cosman | | 600/411 |
| 6,675,040 B1 * | 1/2004 | Cosman | | 600/427 |
| 6,814,575 B2 * | 11/2004 | Poirier | | 433/75 |
| 6,925,198 B2 * | 8/2005 | Scharlack et al. | | 382/128 |
| 6,947,038 B1 * | 9/2005 | Anh et al. | | 345/419 |
| 7,024,237 B1 * | 4/2006 | Bova et al. | | 600/429 |
| 7,123,767 B2 * | 10/2006 | Jones et al. | | 382/154 |
| 7,133,042 B2 * | 11/2006 | Anh et al. | | 345/419 |
| 7,160,110 B2 * | 1/2007 | Imgrund et al. | | 433/213 |
| 2002/0037489 A1 * | 3/2002 | Jones et al. | | 433/24 |
| 2002/0048741 A1 * | 4/2002 | Jordan et al. | | 433/73 |
| 2002/0102517 A1 * | 8/2002 | Poirier | | 433/173 |
| 2002/0156363 A1 * | 10/2002 | Hunter et al. | | 600/410 |
| 2002/0188194 A1 * | 12/2002 | Cosman | | 600/426 |
| 2003/0008259 A1 * | 1/2003 | Kuo et al. | | 433/6 |
| 2003/0039389 A1 * | 2/2003 | Jones et al. | | 382/154 |
| 2003/0187351 A1 * | 10/2003 | Franck et al. | | 600/429 |
| 2004/0096799 A1 * | 5/2004 | Hughes et al. | | 433/24 |
| 2004/0122311 A1 * | 6/2004 | Cosman | | 600/427 |
| 2004/0127788 A1 * | 7/2004 | Arata | | 600/424 |
| 2004/0138556 A1 * | 7/2004 | Cosman | | 600/424 |
| 2004/0157188 A1 * | 8/2004 | Luth et al. | | 433/75 |
| 2004/0167391 A1 * | 8/2004 | Solar et al. | | 600/411 |
| 2004/0167393 A1 * | 8/2004 | Solar et al. | | 600/414 |
| 2004/0172150 A1 * | 9/2004 | Perot et al. | | 700/98 |
| 2005/0037320 A1 * | 2/2005 | Poirier | | 433/173 |
| 2005/0055035 A1 * | 3/2005 | Cosman et al. | | 606/130 |
| 2005/0153255 A1 * | 7/2005 | Sporbert et al. | | 433/24 |
| 2005/0203367 A1 * | 9/2005 | Ahmed et al. | | 600/407 |
| 2005/0203726 A1 * | 9/2005 | Marshall | | 703/11 |
| 2005/0219242 A1 * | 10/2005 | Anh et al. | | 345/419 |
| 2006/0127856 A1 * | 6/2006 | Wen | | 433/213 |
| 2006/0127860 A1 * | 6/2006 | Wen | | 433/213 |
| 2006/0142657 A1 * | 6/2006 | Quaid et al. | | 600/424 |
| 2006/0147100 A1 * | 7/2006 | Fitzpatrick | | 382/131 |
| 2006/0173269 A1 * | 8/2006 | Glossop | | 600/407 |
| 2006/0173293 A1 * | 8/2006 | Marquart et al. | | 600/426 |
| 2006/0241416 A1 * | 10/2006 | Marquart et al. | | 600/432 |
| 2006/0257817 A1 * | 11/2006 | Shelton | | 433/75 |
| 2006/0275731 A1 * | 12/2006 | Wen et al. | | 433/24 |
| 2006/0275736 A1 * | 12/2006 | Wen et al. | | 433/213 |
| 2007/0016008 A1 * | 1/2007 | Schoenefeld | | 600/424 |
| 2007/0031774 A1 * | 2/2007 | Cinader et al. | | 433/24 |
| 2007/0031790 A1 * | 2/2007 | Raby et al. | | 433/213 |
| 2007/0031791 A1 * | 2/2007 | Cinader et al. | | 433/213 |
| 2007/0071176 A1 * | 3/2007 | Main et al. | | 378/207 |
| 2007/0072144 A1 * | 3/2007 | Imgrund et al. | | 433/24 |
| 2007/0141525 A1 * | 6/2007 | Cinader, Jr. | | 433/23 |
| 2007/0225599 A1 * | 9/2007 | Solar et al. | | 600/424 |
| 2007/0238961 A1 * | 10/2007 | Vilsmeier et al. | | 600/407 |
| 2007/0270685 A1 * | 11/2007 | Kang et al. | | 600/424 |
| 2007/0293769 A1 * | 12/2007 | Doherty et al. | | 600/476 |
| 2009/0270723 A1 * | 10/2009 | Kim | | 600/426 |
| 2009/0274990 A1 * | 11/2009 | Kim | | 433/75 |
| 2009/0310832 A1 * | 12/2009 | Kim | | 382/128 |

FOREIGN PATENT DOCUMENTS

| | | |
|---|---|---|
| JP | 2006-141640 A | 6/2006 |
| WO | WO-2006/033483 A1 | 3/2006 |

* cited by examiner

A

B

C

MEDICAL IMAGING MARKER AND PROGRAM FOR UTILIZING SAME

TECHNICAL FIELD

The present invention relates to a medical imaging marker, and a computer program to be used when a medical image acquired through imaging with the use of the medical imaging marker is processed by a computer.

BACKGROUND ART

A medical imaging marker is often used for providing accurate positional information for imaging data when a patient is imaged by means of a medical imaging apparatus such as CT or MRI.

More specifically, when a medical treatment is carried out based on the results of image diagnosis or simulation performed with the use of medical three-dimensional image information acquired through imaging by means of an imaging apparatus such as CT or MRI, a treatment position and a treatment direction specified on an image should be mapped onto an actual object.

Therefore, a reference position and a direction should be able to be correctly defined in a three-dimensional image formed, for example, based on CT image data acquired through the CT imaging. For the correct definition of the reference position in the image, the medical imaging marker should be present in the image.

The medical imaging marker is typically used to identify a reference point in the acquired three-dimensional image. For identification of a center point of the marker, the marker is preferably imaged as having a round shape when the three-dimensional image is viewed in any angular direction. For this reason, a spherical marker is proposed as the medical imaging marker (see, For example, Patent Document 1).
Patent Document 1: JP-A-2006-141640

DISCLOSURE OF THE INVENTION

Problems to be Solved by the Invention

Where the three-dimensional image is formed based on CT image data acquired through imaging with the spherical marker attached to the object, it is difficult to correctly identify the center point of the spherical marker. The identified center point is liable to be slightly offset from an actual center point.

More specifically, the three-dimensional image based on the CT image data is constituted by cubic or cuboidal voxels defined as minimum units of the image. Multi-slice line CT image data has a voxel size of about 400 microns at the minimum. Since the three-dimensional image is constituted by the voxels, a minute configuration having a size less than the voxel size is leveled off on a voxel basis. Therefore, the profile of the spherical marker, which is displayed on a voxel basis, is liable to be distorted. When the center point of the marker is identified, an error on the order of the voxel size is liable to occur. Even if an attempt is made to automatically identify the spherical body (marker) based on a difference in contrast in the displayed three-dimensional image or sectional image, an image of the spherical marker is displayed as a combination of cubic or cuboidal minimum voxels. Therefore, the profile of the marker is not correctly displayed, so that the position of the marker is determined based on the distorted profile. This makes it impossible to correctly identify the center of the spherical body.

In the dental field, for example, an implantation position in a jaw bone is determined based on CT image data through diagnosis for implantation of a dental implant, and an implantation hole is formed by drilling the jawbone with the use of a guide prepared for specifying the position in an oral cavity. At this time, it is important to accurately correlate a positional relationship in the actual oral cavity with a positional relationship in an oral cavity present in an image. If a significant error occurs, the implant implantation hole is formed at an incorrect position. In order to accurately correlate the positional relationship in the actual oral cavity with the positional relationship in the oral cavity present in the image, it is essential to correctly identify the center point of the marker appearing in the image.

In view of the foregoing, it is a principal object of the present invention to provide a medical imaging marker which allows for accurate identification of a reference point (a center point thereof) in a captured image.

It is another object of the present invention to provide a medical imaging marker which ensures improved identification accuracy.

It is further another object of the present invention to provide a computer processing program which allows for accurate identification of a reference point defined by a medical imaging marker (a center point of the marker) in an image acquired by imaging a patient with the use of the marker.

Means for Solving the Problems

According to an inventive aspect of claim 1, there is provided a medical imaging marker, which includes a base composed of a non-imageable material, three spherical members provided in a predetermined positional relationship in the base and each composed of an imageable material, and an auxiliary marker member provided in the base and composed of the imageable material, the auxiliary marker member having linear portions which are disposed parallel to straight lines extending through center points of the three spherical members and each have a predetermined length sufficient to serve as a mark.

According to an inventive aspect of claim 2, the auxiliary marker member includes polygonal or cylindrical columnar auxiliary marker members each having a predetermined length, and disposed so that straight lines connecting the center points of the three spherical members respectively extend through centers of the auxiliary marker members in the medical imaging marker according to claim 1.

According to an inventive aspect of claim 3, the auxiliary marker member is a planar member having two opposed parallel surfaces, and is disposed with the two surfaces thereof being parallel to a plane extending through the center points of the three spherical members in the medical imaging marker according to claim 1.

According to an inventive aspect of claim 4, the base includes an external coordinate system provided on its surface and having a predetermined coordinate relationship with respect to an internal coordinate system defined by the center points of the three spherical members in the medical imaging marker according to any of claims 1 to 3.

According to an inventive aspect of claim 5, the base serves as a guide block which is later machined into a surgical guide in the medical imaging marker according to claim 4.

According to an inventive aspect of claim 6, there is provided a medical imaging marker, which includes three spherical members disposed in a predetermined positional relationship and each composed of an image able material, and a base which fixes the three spherical members in the predetermined positional relationship, the base being composed of a non-imageable material and having facets or edges present on its surface to define linear portions which are respectively disposed parallel to straight lines extending through center points of the three spherical members and each have a predetermined length sufficient to serve as a mark.

According to an inventive aspect of claim 7, the base includes an external coordinate system provided on its surface and having a predetermined coordinate relationship with respect to an internal coordinate system defined by the center points of the three spherical members in the medical imaging marker according to claim 6.

According to an inventive aspect of claim 8, the base serves as a guide block which is later machined into a surgical guide in the medical imaging marker according to claim 6 or 7.

According to an inventive aspect of claim 9, there is provided a medical imaging marker utilization program for utilizing a medical imaging marker as recited in any of claims 1 to 5, the program including: a preliminarily storing step of preliminarily storing geometrical display patterns representing profiles of the three spherical members, the straight lines connecting the center points of the three spherical members and a profile of the auxiliary marker member including the linear portions; an image displaying step of forming a three-dimensional image based on CT image data acquired by imaging a patient who wears the medical imaging marker, and displaying the three-dimensional image and a desired sectional image of the three-dimensional image; a geometrical display pattern displaying step of reading the stored geometrical display patterns and displaying the geometrical display patterns in superposition with the sectional image displayed in the image displaying step; an image adjusting step of adjusting the displayed sectional image in response to input of an adjustment signal; and a coordinate system defining step of acquiring coordinates of the center points of the three spherical members in the adjusted sectional image and defining a reference coordinate system for the three-dimensional image based on the coordinates of the center points of the three spherical members.

According to an inventive aspect of claim 10, there is provided a medical imaging marker utilization program for utilizing a medical imaging marker as recited in any of claims 6 to 8, the program including: a preliminarily storing step of preliminarily storing geometrical display patterns representing profiles of the three spherical members, the straight lines connecting the center points of the three spherical members and straight lines defining the facets or the edges of the linear portions of the base each having the predetermined length sufficient to serve as the mark; an image displaying step of forming a three-dimensional image based on CT image data acquired by imaging a patient who wears the medical imaging marker, and displaying the three-dimensional image and a desired sectional image of the three-dimensional image; a geometrical display pattern displaying step of reading the stored geometrical display patterns and displaying the geometrical display patterns in superposition with the sectional image displayed in the image displaying step; an image adjusting step of adjusting the displayed sectional image in response to input of an adjustment signal; and a coordinate system defining step of acquiring coordinates of the center points of the three spherical members in the adjusted sectional image and defining a reference coordinate system for the three-dimensional image based on the coordinates of the center points of the three spherical members.

Effects of the Invention

According to the inventive aspect of claim 1, the medical imaging marker is configured such that the three spherical members and the auxiliary marker member each composed of the imageable material are provided in the base composed of the non-imageable material. When a three-dimensional image is formed based on CT image data acquired by imaging the patient wearing the medical imaging marker, for example, by a CT imaging apparatus, only images of the three spherical members and the auxiliary marker member appear as an image of the medical imaging marker in the three-dimensional image. The three spherical members can be easily detected, because they are imaged as each having a generally round shape in any angular direction. However, the images of the spherical members are liable to suffer from deformation, expansion and other errors due to a voxel size and image distortion. Therefore, it is difficult to identify the center points of the spherical members only based on the generally spherical images. In this embodiment, however, the linear portions of the auxiliary marker member disposed parallel to the straight lines extending through the center points of the three spherical members and each serving as a mark simultaneously appear in the three-dimensional image. Therefore, the straight lines extending through the center points of the spherical members can be accurately identified with reference to parallelism between the linear portions of the auxiliary marker member and the straight lines extending through the center points of the spherical members. Thus, the center points of the spherical members can be correctly identified.

As described in claim 2, the polygonal or cylindrical columnar auxiliary marker members each having a predetermined length are employed as the auxiliary marker member. The polygonal or cylindrical columnar auxiliary marker members respectively have linear portions which are disposed parallel to the straight lines extending through the center points of the three spherical members and each have a predetermined length sufficient to serve as a mark. Therefore, the linear portions can provide auxiliary lines for correctly identifying the straight lines extending through the center points of the three spherical members.

The positional relationship between the auxiliary marker members and the three spherical members may be defined such that the straight lines connecting the three spherical members respectively extend through the centers of the auxiliary marker members, or such that the straight lines connecting the center points of the three spherical members respectively overlap the linear portions of the auxiliary marker members.

As described in claim 3, the auxiliary marker member may be planar and disposed in a triangular space defined by the three spherical members.

In this case, the planar auxiliary marker member may have a triangular shape, a rectangular shape, a polygonal shape or a round shape as seen in plan. Thus, the orientation of an image in which the medical imaging marker appears can be easily detected. This arrangement is advantageous in that the image can be easily displayed in a specific orientation.

According to the inventive aspect of claim 4, the external coordinate system is provided on the surface of the base. The external coordinate system thus provided has the predetermined coordinate relationship with respect to the internal coordinate system defined by the center points of the three spherical members provided in the base. Therefore, it is possible to define the internal coordinate system of the image based on the center points of the three spherical members in the captured image, and correctly correlate the internal coordinate system of the image with the external coordinate system provided on the base of the actual medical imaging marker. Thus, the captured image can be correctly correlated with an actual object of the patient.

Where the base of the medical imaging marker serves as a guide block which is later machined into a surgical guide as described in claim 5, a treatment site specified through image diagnosis can be correctly mapped onto the actual object.

According to the inventive aspect of claim 6, when a three-dimensional image is formed based on CT image data acquired by imaging the patient wearing the medical imaging marker and a desired sectional image of the three-dimensional image is displayed, the edges or the facets of the base of the medical imaging marker are displayed as the linear portions each having a predetermined length sufficient to serve as a mark in the sectional image. Therefore, where the medical imaging marker described in claim 6 is used, the linear portions of the base serve as reference mark lines for identifying the center points of the three spherical members in the sectional image. Thus, the center points of the three spherical members can be more accurately identified.

According to the inventive aspect of claim 6, the medical imaging marker has a simpler structure than the marker of claim 1, but yet is capable of correctly identifying the center points of the spherical members in the sectional image.

The marker according to the inventive aspect of claim 7 has the same effects as the marker according to the inventive aspect of claim 4.

The marker according to the inventive aspect of claim 8 has the same effects as the marker according to the inventive aspect of claim 5.

According to the inventive aspect of claim 9, the process program is provided, which makes it possible to form the three-dimensional image based on the CT data acquired by imaging the patient wearing the medical imaging marker of any of claims 1 to 5, and accurately identify three points defined by the marker, i.e., the center points of the three spherical members, in the three-dimensional image or the sectional image of the three-dimensional image.

According to the inventive aspect of claim 10, the process program is provided, which makes it possible to correctly identify the center points of the spherical members when the medical imaging marker of any of the claims 6 to 8 is used.

Thus, the present invention provides the medical imaging markers which are capable of accurately correlating the captured image and the actual object at a higher level of accuracy, and ensure that the treatment can be effectively performed at a clinical site.

Figure 1:
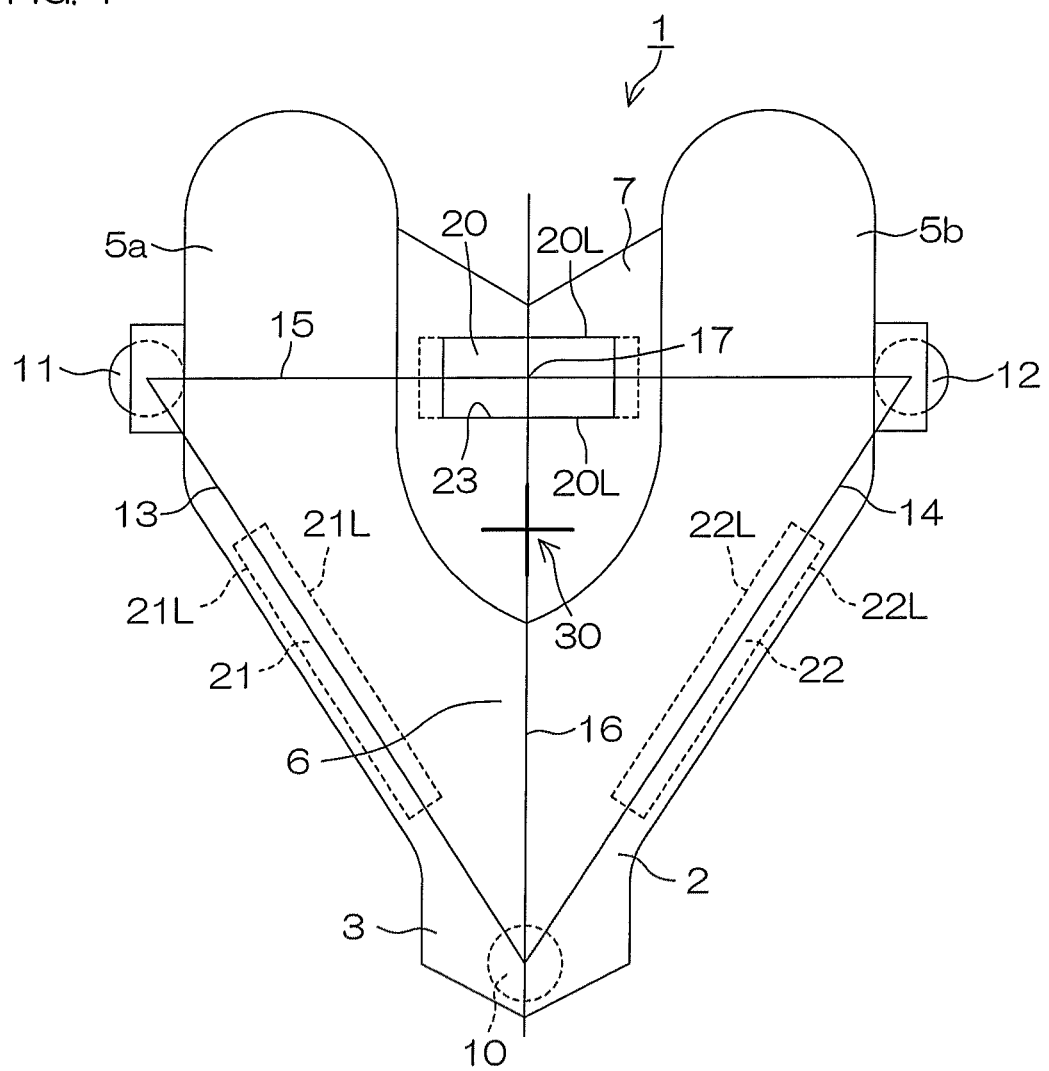
FIG. 1 is a plan view of a medical imaging marker 1 according to one embodiment of the present invention.

Description of Reference Characters 1, 61, 71, 81: Medical imaging markers (markers)
2: Base
10: Front spherical member
11: Right spherical member
12: Left spherical member
20, 21, 22, 63, 82: Auxiliary marker members
30: External coordinate system

BEST MODE FOR CARRYING OUT THE INVENTION

Specific embodiments of the present invention will hereinafter be described in detail with reference to the drawings.

Figure 2:
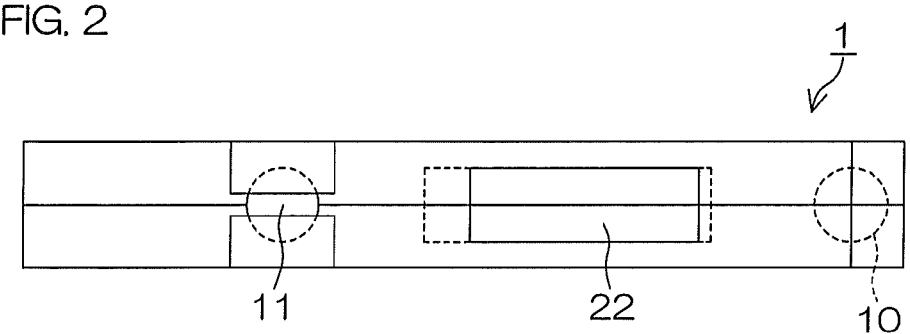
FIG. 2 is a side view of the marker 1.
Figure 3:
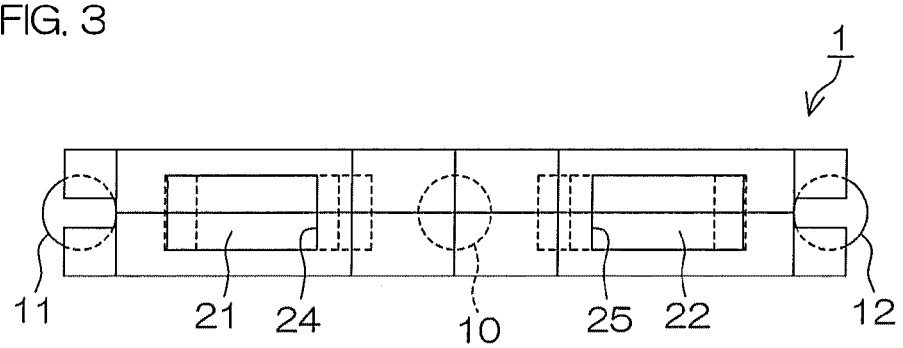
FIG. 3 is a front view of the marker 1.
Figure 4:
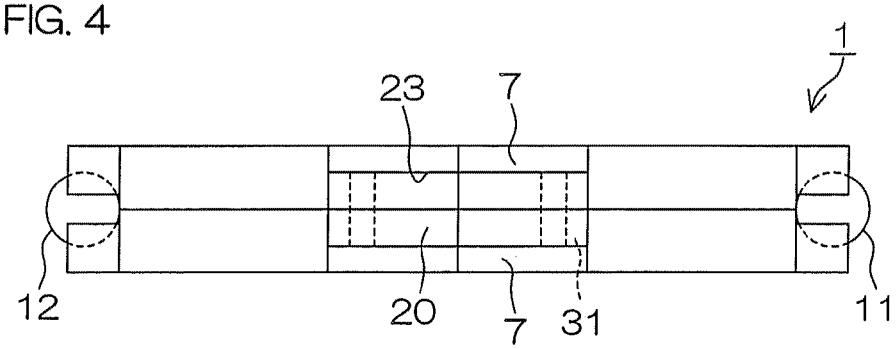
FIG. 4 is a rear view of the marker 1.

FIG. 1 is a plan view of a medical imaging marker (hereinafter referred to simply as "marker") 1 according to one embodiment of the present invention, and FIG. 2 is a side view of the marker 1. FIG. 3 is a front view of the marker 1, and FIG. 4 is a rear view of the marker 1.

Referring to FIGS. 1 to 4, the marker 1 includes a planar base 2 composed of a material having a non-imageable property (non-imageable material) such as an acryl resin.

The marker 1 is fitted in a mouth of a patient, and is used for acquiring CT image data by imaging an oral cavity of the patient by means of a CT imaging apparatus. The base 2 of the marker 1 has a generally U-shape as seen in plan. That is, the base 2 includes a generally U-shaped portion including a right rear planar portion 5a to be held between upper and lower right back teeth, a left rear planar portion 5b to be held between upper and lower left back teeth, and a front planar portion 6 to be held between upper and lower side-to-front teeth. A portion of the base 2 present between the planar portions 5a and 5b is defined as a tongue portion 7 having a reduced thickness. In this embodiment, left and right side surfaces of the front planar portion 6 are flat, and laterally opposite portions of the front planar portion 6 are tapered toward a front middle portion of the base as seen in plan. The front planar portion 6 includes a distal projection 3 provided at its distal end. The base 2 includes a pair of base pieces each having the aforementioned plan shape and bonded to each other.

The marker 1 includes three spherical members 10, 11, 12, i.e., a front spherical member 10 disposed in the distal projection 3 of the base 2, a right spherical member 11 disposed as being bulged from a right side surface of the right rear planar portion 5a of the base 2, and a left spherical member 12 disposed as being bulged from a left side surface of the left rear planar portion 5b of the base 2. The spherical members 10, 11, 12 are each composed of a material having an imageable property (imageable material) such as aluminum. In this embodiment, the three spherical members 10, 11, 12 are disposed in a positional relationship such that straight lines 13, 14, 15 connecting center points of the three spherical members 10, 11, 12 define an isosceles triangle with the front spherical member 10 being defined as an apex and with the straight lines 13, 14 having the same length and symmetrical angles.

The marker 1 further includes auxiliary marker members 20, 21, 22. The auxiliary marker members 20, 21, 22 are also composed of the imageable material such as aluminum. In this embodiment, the auxiliary marker members 20, 21, 22 each have an elongated rectangular columnar shape (elongated plate shape).

More specifically, the auxiliary marker member 20 is disposed so that the straight line 15 connecting the center points of the right spherical member 11 and the left spherical member 12 extends through a center of the auxiliary marker member 20 longitudinally of the auxiliary marker member 20. The auxiliary marker member 20 has linear portions 20L disposed parallel to the straight line 15 and each having a predetermined length sufficient to serve as a mark when a positioning operation to be described later is performed.

The auxiliary marker member 21 is disposed so that the straight line 13 connecting the center points of the front spherical member 10 and the right spherical member 11 extends through a center of the auxiliary marker member 21 longitudinally of the auxiliary marker member 21. The auxiliary marker member 21 has linear portions 21L disposed parallel to the straight line 13 and each having a predetermined length sufficient to serve as a mark.

The auxiliary marker member 22 is disposed so that the straight line 14 connecting the center points of the front spherical member 10 and the left spherical member 12 extends through a center of the auxiliary marker member 22 longitudinally of the auxiliary marker member 22. The auxiliary marker member 22 has linear portions 22L disposed parallel to the straight line 14 and each having a predetermined length sufficient to serve as a mark.

The marker 1 further includes an external coordinate system 30 provided on a surface of the base 2. The external coordinate system 30 provides a reference point (origin) on the basis of which the base 2 is set in a machining apparatus (e.g., a CAM apparatus) and machined into a surgical guide.

On the other hand, the marker 1 defines an internal coordinate system thereof based on the three spherical members 10, 11, 12 provided in the base 2. Where a plane extending through the center points of the three spherical members 10, 11, 12 is defined as a reference plane, for example, the straight line 15 extending through the center points of the right spherical member 11 and the left spherical member 12 in the reference plane is defined, for example, as an X-axis. Further, a straight line extending through a middle point of the straight line 15 perpendicularly to the straight line 15 in the reference plane (a straight line 16 extending through the center point of the front spherical member 10) is defined as a Y-axis. Further, a straight line (not shown) extending through an intersection 17 of the straight line 15 (X-axis) and the straight line 16 (Y-axis) perpendicularly to the straight lines 15, 16 is defined as a Z-axis.

The X-, Y- and Z-axes of the internal coordinate system may be defined based on straight lines other than the aforementioned straight lines.

In this embodiment, the X-, Y- and Z-axes of the internal coordinate system are disposed in a predefined positional relationship with respect to the external coordinate system 30. Therefore, coordinates based on the internal coordinate system can be easily converted into coordinates based on the external coordinate system 30 by a predefined coordinate conversion expression.

In this embodiment, a window 23 is provided in the tongue portion 7 of the base 2 for exposing the auxiliary marker member 20 as seen in plan (or from a rear side). The window 23 makes it easier to remove the auxiliary marker member 20 before the base 2 is machined. The auxiliary marker member 20 may be unexposed and buried in the base 2 without the provision of the window 23.

The auxiliary marker members 21, 22 are also partly exposed through windows 24, 25 provided in the side surfaces for easy removal of the auxiliary marker members 21, 22 prior to the machining of the base 2. However, the marker 1 may be configured without the provision of the windows 24, 25.

Similarly, the right spherical member 11 and the left spherical member 12 are each held by projections of the base 2 from upper and lower sides, and partly exposed. This allows for easy removal of the right spherical member 11 and the left spherical member 12 prior to the machining of the base 2. Like the front spherical member 10, the right spherical member 11 and the left spherical member 12 may be entirely buried in the base 2 rather than have the aforementioned configuration.

Figure 5:
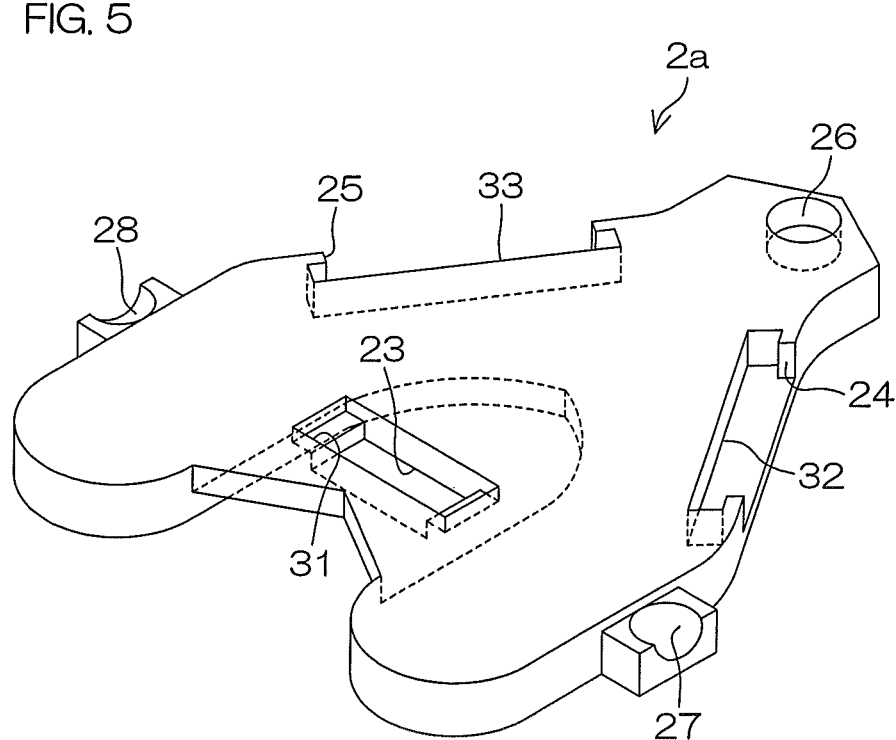
FIG. 5 is a perspective view of one 2a of paired base pieces of a base 2 of the marker 1.

FIG. 5 is a perspective view of one 2a of the paired base pieces of the base 2 of the marker 1. The base piece 2a is unitarily formed of, for example, an acryl resin by an injection molding method, and includes a recess 26 for accommodating the front spherical member, a recess 27 for accommodating the right spherical member, a recess 28 for accommodating the left spherical member, a recess 31 for accommodating the auxiliary marker member 20, a recess 32 for accommodating the auxiliary marker member 21 and a recess 33 for accommodating the auxiliary marker member 22. The recesses 31, 32, 33 are respectively formed with the windows 23, 24 25. When the auxiliary marker members 20, 21, 22 are removed from the recesses, the windows 23, 24, 25 are expanded (or broken).

The other base piece is configured vertically symmetrically with respect to the base piece 2a, and inverted with respect to the base piece 2a. The three spherical members 10, 11, 12 and the three auxiliary marker members 20, 21, 22 are respectively fitted in the recesses 26, 27, 28, 31, 32, 33, and the paired base pieces are bonded together in superposition, whereby the marker 1 is completed.

The paired base pieces may be combined together by engaging engagement recesses and projections respectively formed in the paired base pieces rather than bonding the paired base pieces in superposition.

Figure 6:
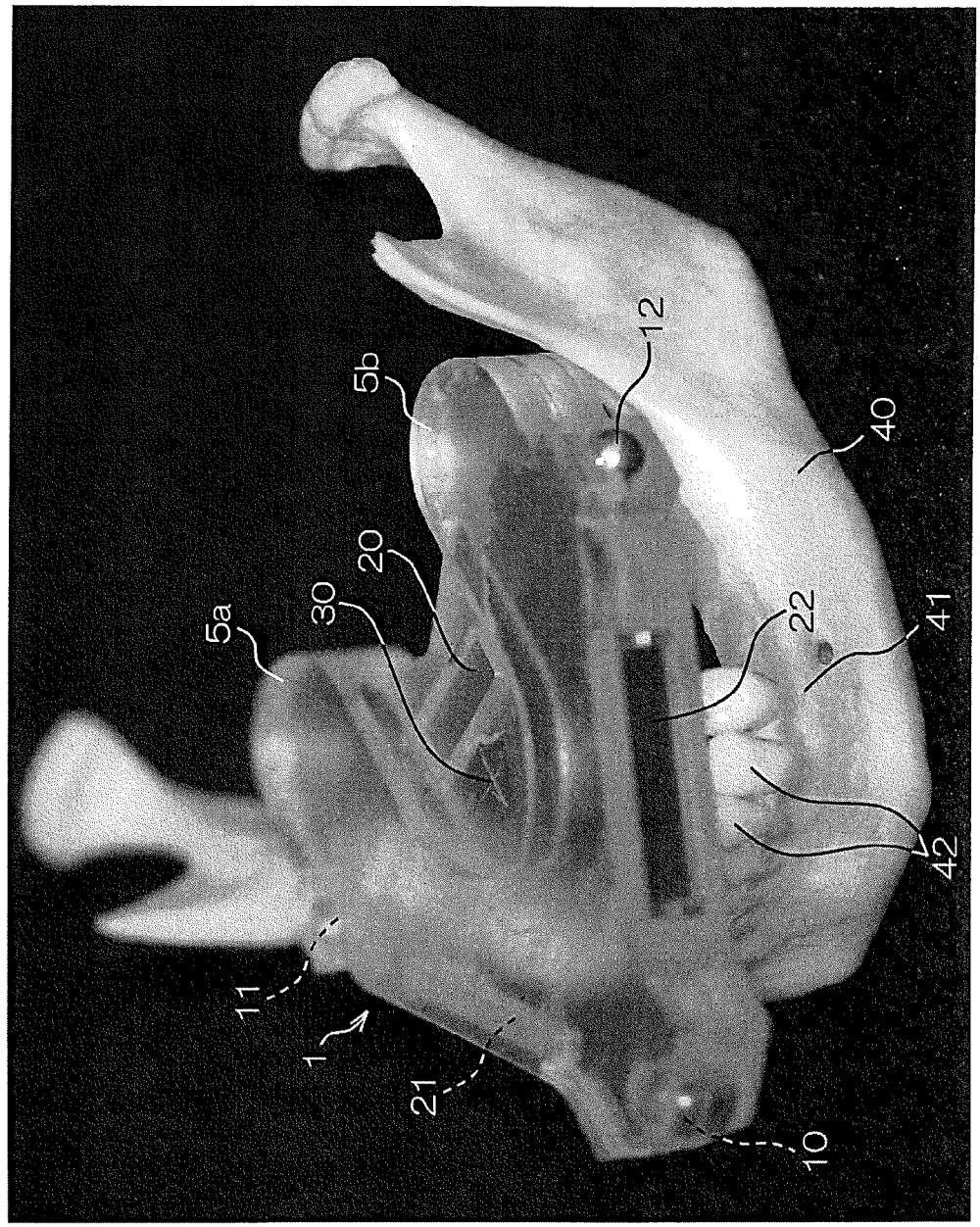
FIG. 6 is a perspective view illustrating a state of the marker 1 fitted in a human dental arch model according to the embodiment of the present invention.

FIG. 6 is a perspective view illustrating a state of the marker 1 fitted on a human dental arch model according to this embodiment. In FIG. 6, a reference numeral 40 denotes a dental arch model including a lower jaw 41 and teeth 42, and the marker 1 is fitted on the dental arch model 40. The marker 1 is fitted on the model 40 in a manner such that the rear planar portions 5a, 5b are accommodated in an inner portion of the dental cavity.

In practice, the marker 1 is not fitted in the dental arch model 40 but fitted in the oral cavity of the patient, and the face and the oral cavity of the patient are imaged by means of the CT imaging apparatus.

Figure 7:
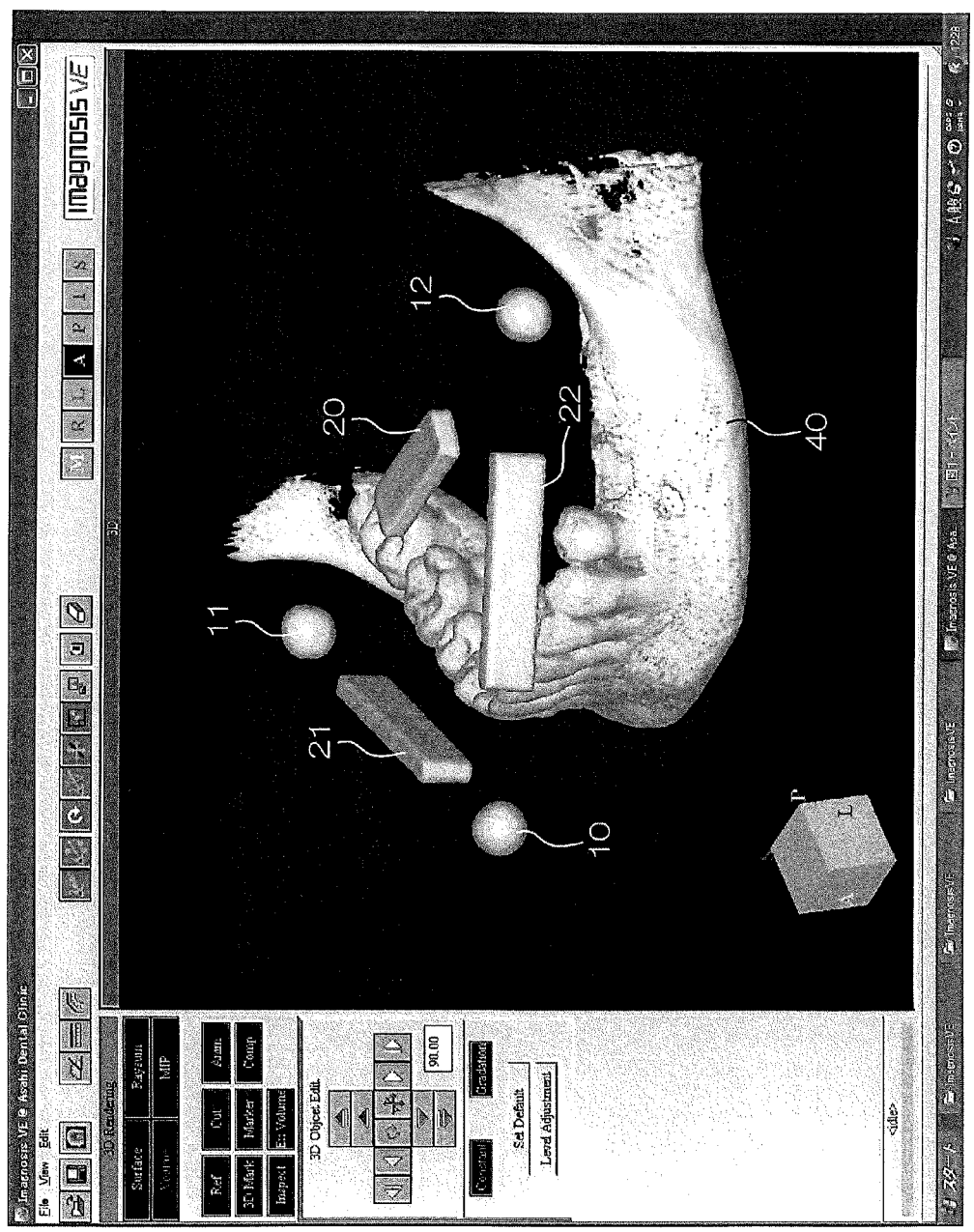
FIG. 7 is a diagram showing a three-dimensional image formed on the basis of CT image data acquired by imaging a dental arch model 40 fitted with the marker 1 of FIG. 6 by a CT imaging apparatus and displayed on a display device of a computer.

FIG. 7 is a diagram showing a three-dimensional image formed on the basis of CT image data acquired by imaging the dental arch model 40 fitted with the marker 1 of FIG. 6 by the CT imaging apparatus and displayed on a display device of a computer. As shown in FIG. 7, the base 2 of the marker 1 does not appear in the three-dimensional image, and the three spherical members 10, 11, 12 and the three auxiliary marker members 20, 21, 22 each composed of the imageable material and provided in the base 2 are displayed above the dental arch model 40 in levitation.

Figure 8:
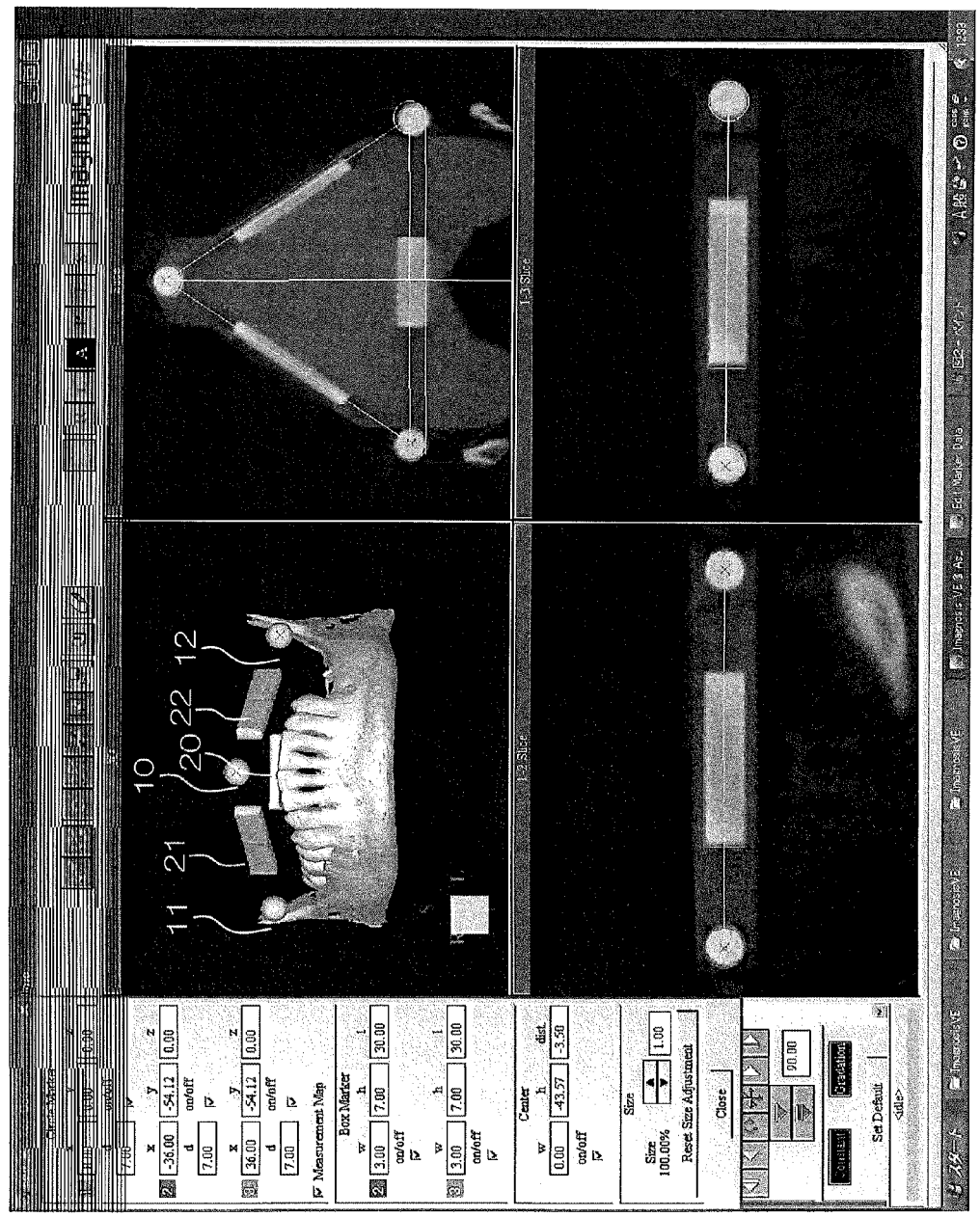
FIG. 8 is a diagram showing a display screen on which three sectional images are simultaneously displayed in addition to the three-dimensional image by way of example.

Then, as shown in FIG. 8, three sectional images are simultaneously displayed in addition to the three-dimensional image by operating a keyboard or a mouse connected to the computer. For example, the three-dimensional image is displayed in an upper left part, and the sectional images are displayed in an upper right part, a lower left part and a lower right part.

This display operation is performed in the following manner. The three-dimensional image is first rotated to an angular orientation that allows for easy viewing, and possible center points of the front spherical member 10, the right spherical member 11 and the left spherical member 12 are specified by a cursor. The specified points are indicated by crisscross marks in FIG. 8.

Then, a horizontal sectional image extending through the center points of the front spherical member 10, the right spherical member 11 and the left spherical member 12 (the specified points indicated by the crisscross points) is displayed in the upper right part. Further, a vertical sectional image extending through the center point of the front spherical member 10 and the center point of the right spherical member 11 is displayed in the lower right part, and a vertical sectional image extending through the center point of the front spherical member 10 and the center point of the left spherical member 12 is displayed in the lower left part.

At this time, geometrical display patterns (circles and lines) representing the profiles of the three spherical members (the front spherical member 10, the right spherical member 11 and the left spherical member 12), the straight lines connecting the center points of the three spherical members 10, 11, 12 and the profiles of the auxiliary marker members 20, 21, 22 including the linear portions are read out of the computer, and displayed in the sectional images. The geometrical display patterns are displayed in a manner such that center points of the geometrical display patterns of the three spherical members substantially coincide with the center point of the front spherical member 10, the center point of the right spherical member 11 and the center point of the left spherical member 12 specified in the three-dimensional image.

However, the possible center points of the spherical members 10, 11, 12 specified in the three-dimensional image are not necessarily correct center points. That is, the geometrical display patterns superposed on the three sectional images are often positionally offset from the front spherical member 10, the right spherical member 11 and the left spherical member 12 and the auxiliary marker members 20, 21, 22, and the profiles of the sections of the three spherical members 10, 11, 12 do not necessarily coincide with the profiles of the geometrical display patterns of the spherical members (see the front spherical member 10 and the right spherical member 11 in the upper right sectional image, and the front spherical member 10 in the lower right sectional image in FIG. 8). This is because the three-dimensional image is constituted by voxels based on the CT image data, and the voxels each have a size of about 400 microns at the minimum. Therefore, the spherical members 10, 11, 12 are each unlikely to have a perfectly round profile, but each likely to have a distorted profile or an offset circular profile.

Thus, sectional images of the front spherical member 10, the right spherical member 11 and the left spherical member 12 are not displayed as each having a perfectly round profile, but having a distorted profile represented on a voxel basis. This makes it difficult to accurately identify the center points of the spherical members.

In this embodiment, therefore, the geometrical display patterns are displayed in superposition with the sectional images. With reference to the linear portions of the auxiliary marker members 20, 21, 22, the sectional images thus displayed are adjusted so that the linear portions of the auxiliary marker members 20, 21, 22 are disposed parallel to the straight lines of the geometrical display patterns, and the sections of the spherical members 10, 11, 12 coincide with the profiles of the geometrical display patterns of the spherical members. Then, the center points of the spherical members 10, 11, 12 subjected to the positional adjustment are identified and stored.

Figure 9:
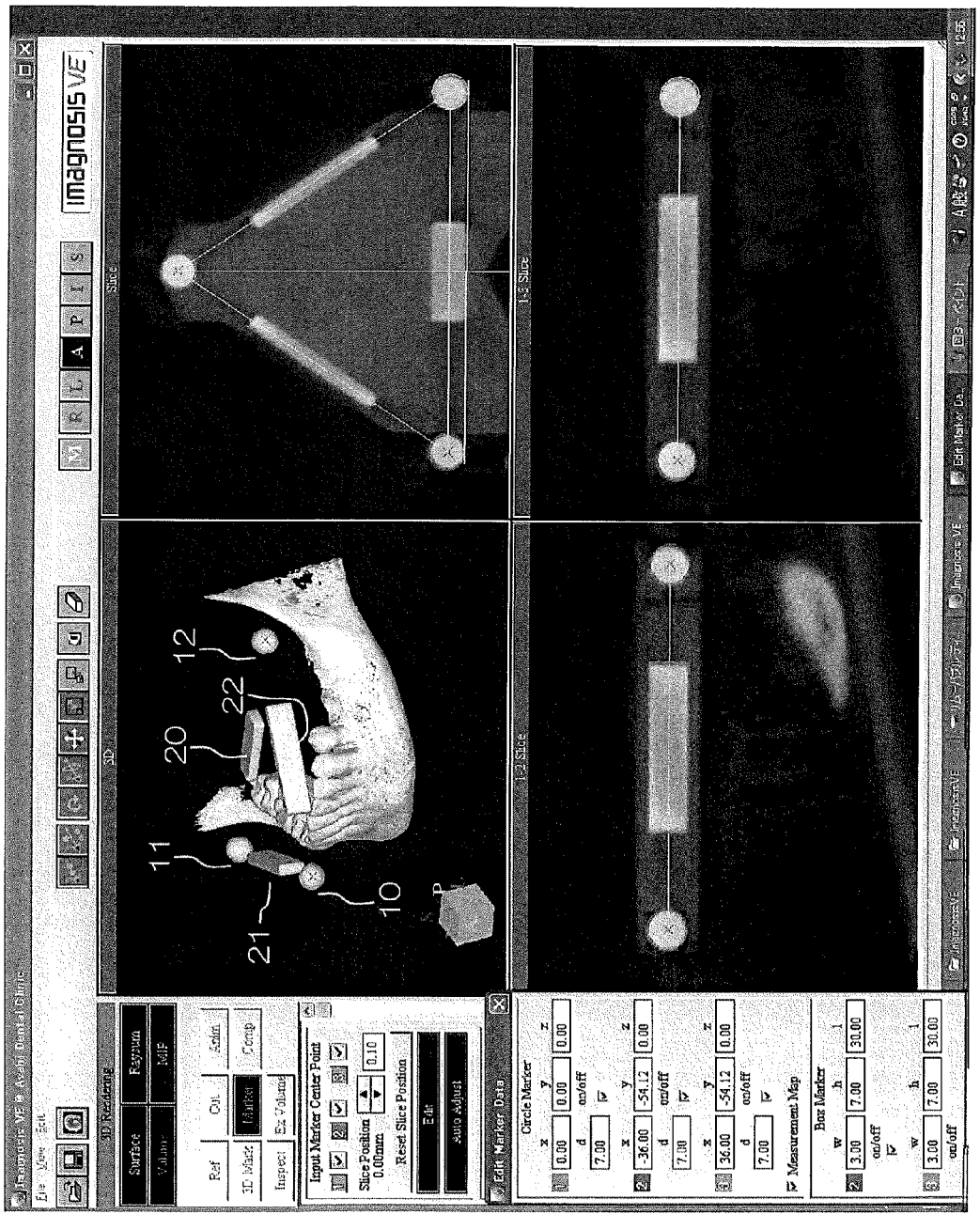
FIG. 9 is a diagram showing a display screen on which the sectional images of FIG. 8 are displayed with center points of spherical members being adjusted.

FIG. 8 shows positional relationships between the sectional images and the geometrical display patterns before the positional adjustment of the sectional images, and FIG. 9 shows positional relationships between the sectional images and the geometrical display patterns after the adjustment. In FIG. 9, the three-dimensional image in the upper left part is illustrated as viewed in a different angular direction.

In this manner, the center points of the three spherical members 10, 11, 12 of the marker can be accurately identified in the three-dimensional image, particularly in the sectional images. With the center points of the three spherical members 10, 11, 12 thus identified, the internal coordinate system of the marker 1, i.e., the reference coordinate system of the displayed three-dimensional image, can be accurately defined based on the three points.

Figure 10:
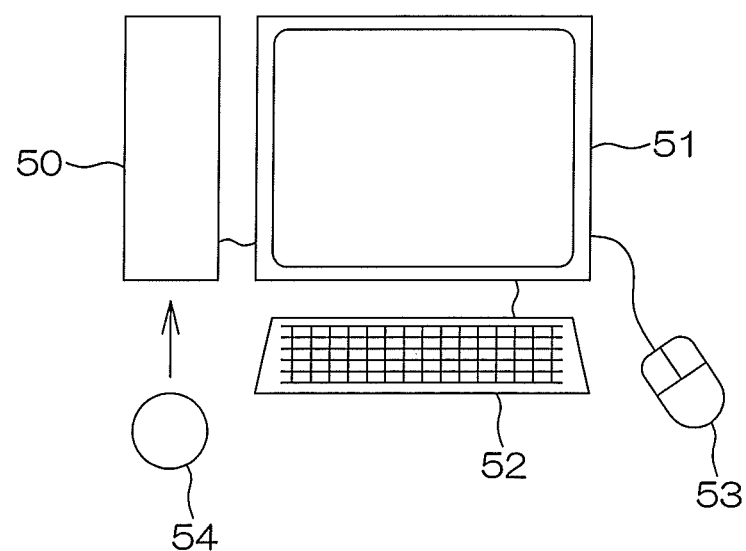
FIG. 10 is a diagram showing the schematic configuration of a computer which runs a program according to another embodiment of the present invention.
Figure 11:
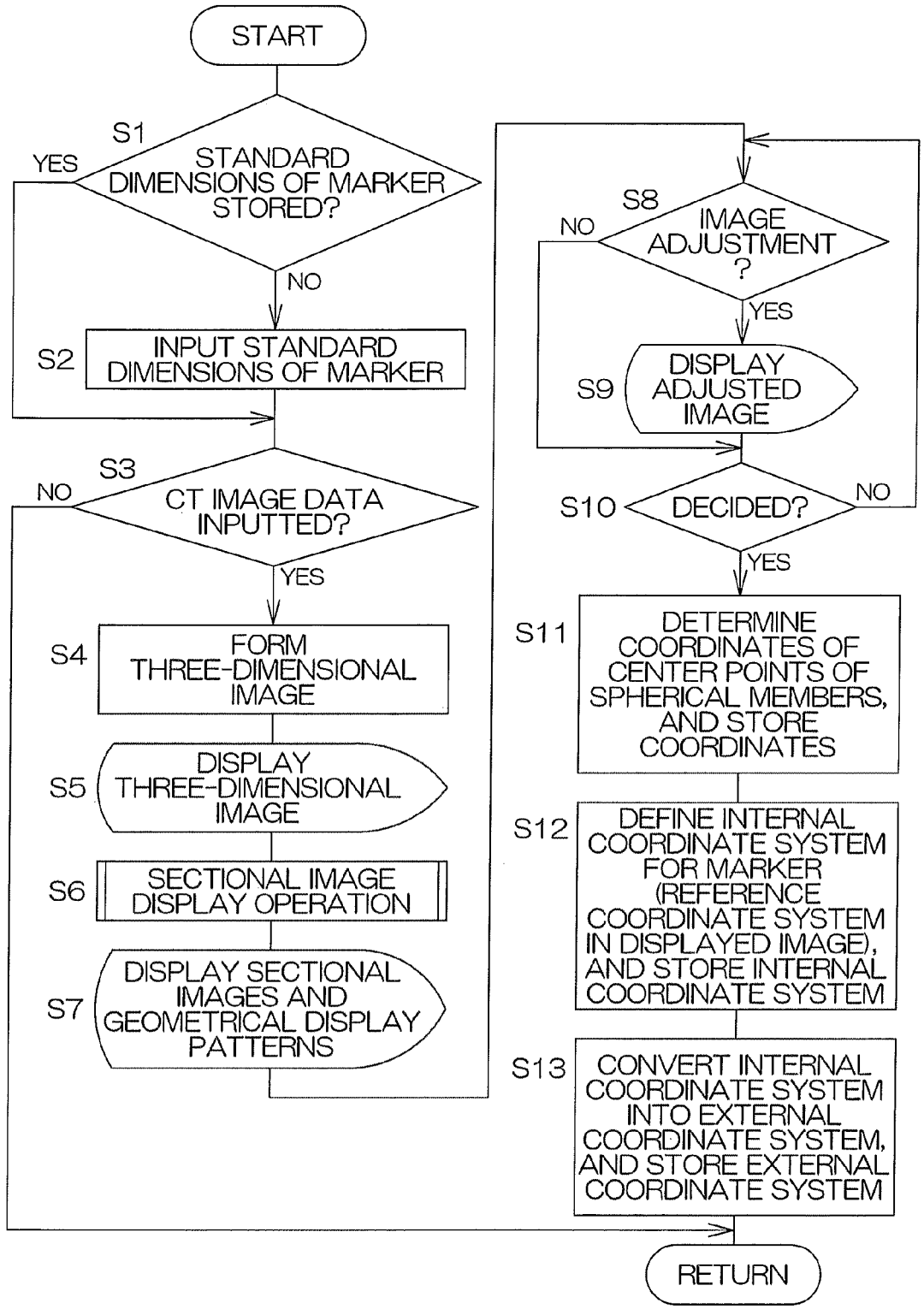
FIG. 11 is a flow chart for explaining a process to be performed based on the program according to the embodiment of the invention.
Figure 12:
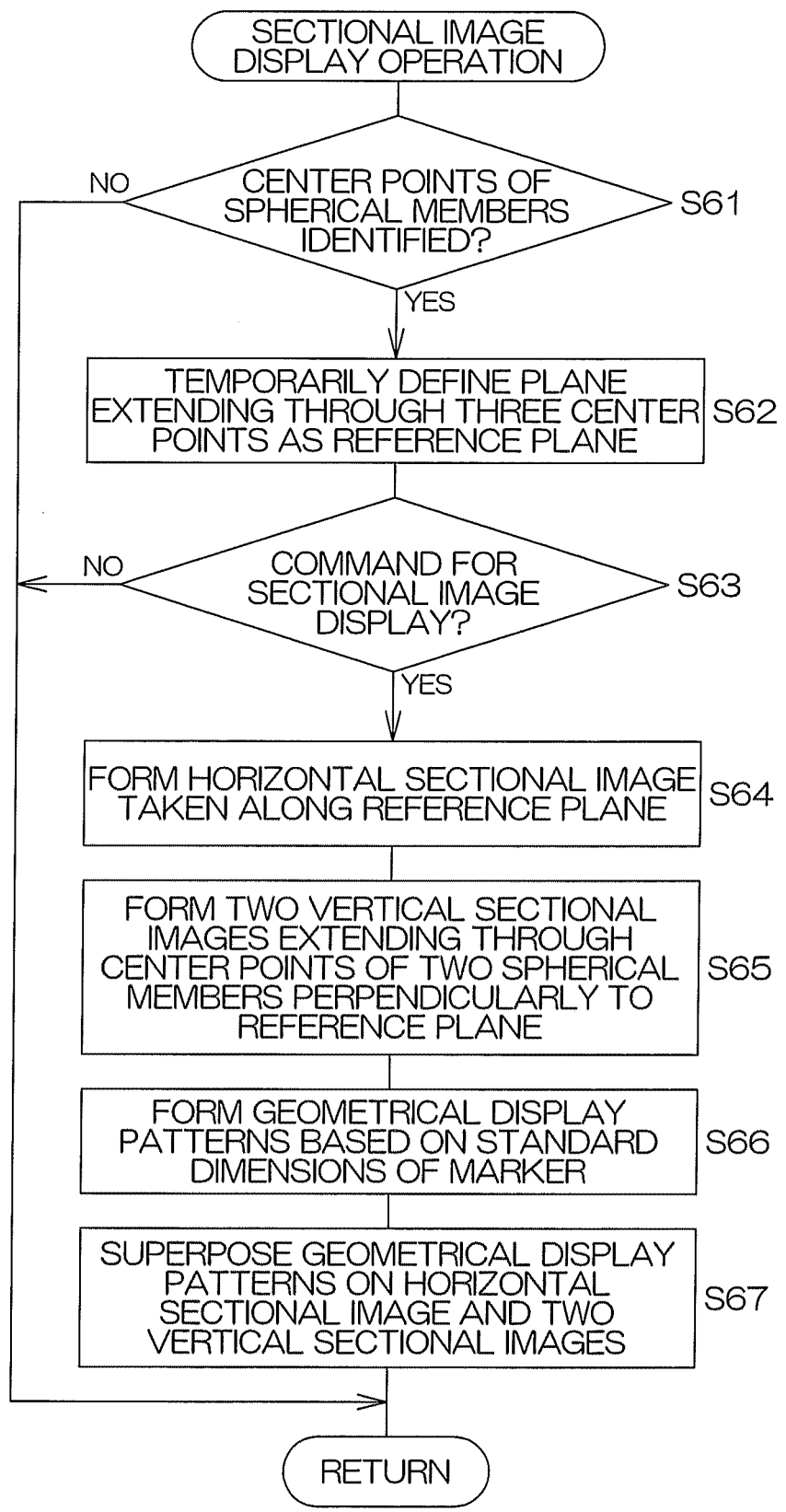
FIG. 12 is a flow chart for explaining a process to be performed based on the program according to the embodiment of the present invention.

FIGS. 10 to 12 are diagrams for explaining a program for utilizing the marker 1 according to the embodiment of the present invention. FIG. 10 is a diagram showing the schematic configuration of a computer which operates based on a program installed therein. FIGS. 11 and 12 are flow charts for explaining a process to be performed based on the program.

As shown in FIG. 10, the computer may be a general-purpose microcomputer. The computer is merely required to include a microcomputer main body 50 including a CPU, a hard disk and the like, a display device 51, a keyboard 52, a mouse 53 and the like. The main body 50 is capable of reading CT image data, for example, stored in a CD-ROM 54.

FIG. 11 is a flow chart for explaining a process to be performed by a control circuit of the CPU and the like in the main body 50 based on a marker utilization program. Referring to FIG. 11, the marker utilization program will be described.

When the process is started, it is first judged if the standard dimensions of the marker 1 are stored (Step S1). If the standard dimensions of the marker 1 are not stored, the standard dimensions of the marker 1 are inputted and stored (Step S2).

The standard dimensions of the marker 1 include the diameters and positional relationship of the front spherical member 10, the right spherical member 11 and the left spherical member 12 of the marker 1 described with reference to FIG. 1, the exterior dimensions of the auxiliary marker members 20, 21, 22, the positional relationships of the auxiliary marker members 20, 21, 22 with respect to the three spherical members 10, 11, 12, and the positional relationships of the three spherical members 10, 11, 12 with respect to the external coordinate system 30, and may further include the dimensions of the base 2.

The standard dimensions of the marker 1 are thus preliminarily stored, so that the geometrical display patterns of the marker 1 can be displayed on the display device 51 based on the standard dimensions.

Next, it is judged if CT image data is inputted (Step S3). If the CT image data is inputted to the main body 50, a three-dimensional image is formed based on the inputted CT image data (Step S4), and the formed three-dimensional image is displayed on the display device 51 (Step S5).

Then, a sectional image display operation is performed (Step S6). The sectional image display operation is shown in detail in a flow chart of FIG. 12.

Referring to FIG. 12, it is judged if the center points of the three spherical members 10, 11, 12 are specified in the three-dimensional image (see FIG. 7) displayed on the display device 51 in the sectional image display operation (Step S61). When the center points of the three spherical members 10, 11, 12 are specified, a plane extending through the specified three center points is defined as a temporary reference plane (Step S62).

In response to a command signal thereafter applied for displaying sectional images (when the keyboard 52 or the mouse 53, for example, is operated to apply a command signal for displaying sectional images) (Step S63), a horizontal sectional image cut along the temporary reference plane is formed (Step S64). Then, two types of vertical sectional images are formed as extending through center points of two spherical members 10, 11; 10, 12; or 11, 12 perpendicularly to the temporary reference plane (Step S65).

Further, geometrical display patterns are formed based on the standard dimensions of the marker 1 (Step S66). Then, images to be displayed are formed by superposing the geometrical display patterns on the horizontal sectional image and the two vertical sectional images (Step S67).

Referring again to FIG. 11, the sectional images to be displayed and the geometrical display patterns to be displayed in superposition with the sectional images are prepared by performing the sectional image display operation described with reference to FIG. 12 in Step S6. Then, the sectional images and the geometrical display patterns are displayed in superposed relation (Step S7). Exemplary display images are the horizontal sectional image in the upper right part, the vertical sectional image in the lower left part and the vertical sectional image in the lower right part shown in FIG. 8.

In turn, it is judged if an image adjustment signal is applied in response to an image adjustment command operation performed by a user (Step S8). If the images are adjusted, the adjusted images are displayed (Step S9). The adjusted images are, for example, the horizontal sectional image displayed in the upper right part, the vertical sectional image displayed in the lower left part and the vertical sectional image displayed in the lower right part in FIG. 9.

If a decision signal is inputted by pressing a predetermined key of the keyboard after the adjustment of the images (Step S10), the coordinates of the center points (indicated by the crisscross marks) of the spherical members 10, 11, 12 in the sectional images shown in FIG. 9 are determined as center point coordinates and stored (Step S11).

Based on the coordinates of the center points thus determined, the internal coordinate system of the marker 1 (in other words, the reference coordinate system for the images displayed on the display device 51) is defined and stored (Step S12).

Then, the stored internal coordinate system is converted into the external coordinate system (Step S13). The internal coordinate system defined in Step S12 is based on the center points of the imaged spherical members 10, 11, 12, and serves as the reference coordinate system on a display screen. Since the reference coordinate system on the display screen cannot be used as a reference coordinate system for actually machining the base 2 of the marker 1, the coordinate conversion is required. In this embodiment, the internal coordinate system is automatically converted into the external coordinate system 30. Therefore, the external coordinate system resulting from the conversion is applied as it is to the machining apparatus (e.g., the CAM apparatus) when the base 2 of the marker 1 is actually machined. Thus, the base 2 can be machined into a desired configuration.

In other words, the internal coordinate system defined based on the three spherical members 10, 11, 12 is a reference coordinate system which serves as a reference for handling the images displayed on the display device 51, while the external coordinate system 30 provided on the surface of the marker 1 is a coordinate system which serves as a reference for correlating the images with an actual object to define the position of the actual object. The conversion of the internal coordinate system to the external coordinate system 30 makes it possible to correctly correlate the images with the actual object based on the external coordinate system 30 of the marker 1.

The external coordinate system for the correlation provides positional data which can be directly used when the marker 1 is thereafter machined by the machining apparatus (e.g., the CAM apparatus). The base 2 of the marker 1 can be machined into a desired guide configuration on the basis of the data converted based on the external coordinate system.

Figure 13:
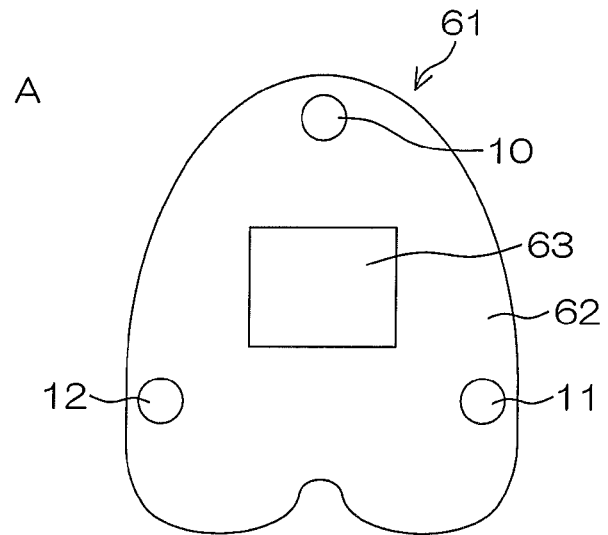
FIGS. 13A, 13B and 13C are schematic diagrams showing other examples of the inventive medical imaging marker.
Figure 13:
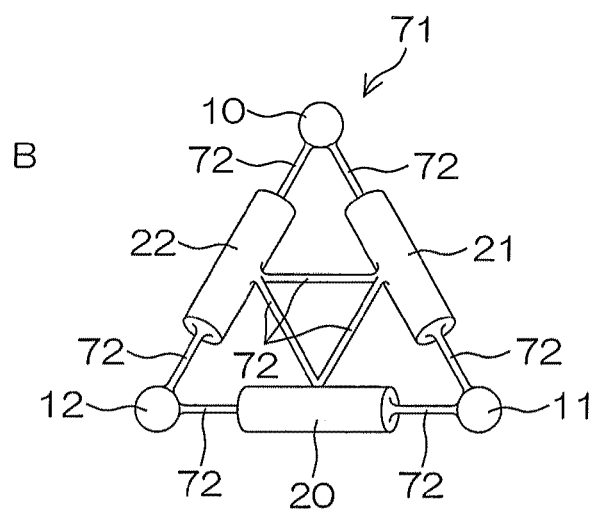
Figure 13:
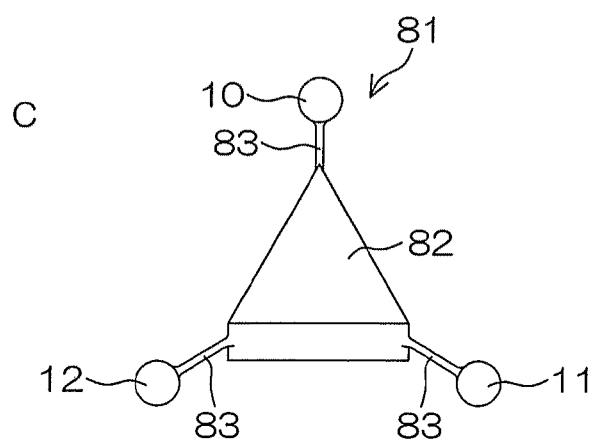

FIGS. 13A, 13B and 13C are schematic diagrams showing other examples of the inventive medical imaging marker.

The medical imaging marker may be embodied as a marker 61 shown in FIG. 13A, a marker 71 shown in FIG. 13B, or a marker 81 shown in FIG. 13C.

More specifically, as shown in FIG. 13A, the marker 61 is configured such that three spherical members 10, 11, 12 composed of an imageable material are buried in a predetermined relationship in a base 62 composed of a non-imageable material, and an auxiliary marker member 63, for example, having a rectangular plan shape is disposed in a predetermined positional relationship with respect to the three spherical members 10, 11, 12. The auxiliary marker member 63 is a thin plate having a square plan shape and composed of an imageable material such as aluminum. The auxiliary marker member 63 has a front surface, a rear surface and side surfaces which are defined as linear portions each having a predetermined length. The linear portions serve as auxiliary marks for defining the center points of the three spherical members 10, 11, 12.

In FIG. 13A, the plan shape of the auxiliary marker member 63 is not limited to the rectangular shape, but may be any other polygonal shape, or a circular or oval shape. Where the auxiliary marker member 63 has a circular or oval plan shape, the two opposite surfaces of the auxiliary marker member 63 serve as linear portions each having a predetermined length.

The marker 71 shown in FIG. 13B does not include a base in which three spherical members 10, 11, 12 are otherwise provided. The three spherical members 10, 11, 12 and three auxiliary marker members 20, 21, 22 are disposed in a predetermined positional relationship, and connected to one another by connection members 72. In this embodiment, the auxiliary marker members 20, 21, 22 each have an elongated cylindrical columnar shape, but may have a polygonal columnar shape.

The marker 81 shown in FIG. 13C includes an auxiliary marker member 82 having a triangular planar shape as seen in plan. Three spherical members 10, 11, 12 are connected to the auxiliary marker member 82 by connection members 83. In this embodiment, the plan shape of the auxiliary marker member 82 is not limited to the triangular shape, but may be a rectangular shape or any other polygonal shape, or a circular or oval shape.

The present invention is not limited to the embodiments described above, but various modifications may be made within the scope of the appended claims.

What is claimed is:

1. A medical imaging marker for use with imaging device, comprising:
    a base composed of a non-imageable material that is substantially invisible to the imaging device, the base having a front portion and a rear portion that is configured to fit into the mouth of a human patient;
    first and second spherical members provided in a predetermined positional relationship in the rear portion of the base and both composed of an imageable material; and
    a third spherical member provided in the front portion of the base in a predetermined positional relationship with the first and second spherical members, the third spherical member being composed of imageable material;
    first, second, and third auxiliary marker members provided in the base and composed of the imageable material, the auxiliary marker members having linear portions and each auxiliary marker member having a predetermined length sufficient to serve as a mark,
    wherein the first auxiliary marker member is disposed in the rear portion of the base and parallel to an axis extending through center points of the first and second spherical members,
    wherein the second auxiliary marker member is disposed parallel to an axis extending through center points of the second and third spherical members, and
    wherein the third auxiliary marker member is disposed parallel to an axis extending through center points of the third and first spherical members.

2. A medical imaging marker as set forth in claim 1, wherein the auxiliary marker member includes polygonal or cylindrical columnar auxiliary marker members each having a predetermined length and being disposed so that the axes connecting the center points of the three spherical members respectively extend through centers of the auxiliary marker members.

3. A medical imaging marker as set forth in claim 1, wherein the auxiliary marker members are planar members having two opposed parallel surfaces, and wherein each of the auxiliary marker members is disposed with the two surfaces thereof being parallel to a plane extending through the center points of the three spherical members.

4. A medical imaging marker as set forth in claim 1, wherein the base includes an external coordinate system provided on its surface and having a predetermined coordinate relationship with respect to an internal coordinate system defined by the center points of the three spherical members.

5. A medical imaging marker as set forth in claim 4, wherein the base serves as a guide block which is later machined into a surgical guide.

6. A medical imaging marker utilization method for use with an imaging device, the method utilizing a medical imaging marker that includes a base composed of a non-imageable material that is substantially invisible to the imaging device and having a front portion and a rear portion that is configured to fit into the month of a human patient, first and second spherical members provided in a predetermined positional relationship in rear portion of the base and both composed of an imageable material a third spherical member composed of imageable material and provided in the front portion of the base in a predetermined positional relationship with the first and second spherical members, and first, second, and third auxiliary marker members provided in the base and composed of the imageable material, the auxiliary marker members having linear portions and each auxiliary marker member having a predetermined length sufficient to serve as a mark, the first auxiliary marker member being disposed in the rear portion of the base and parallel to an axis extending through center points of the first and second spherical members, the second auxiliary marker member being disposed parallel to an axis extending through center points of the second and third spherical members, and the third auxiliary marker member being disposed parallel to an axis extending through center points of the third and first spherical members, said method comprising:
    placing the rear portion of the base in the month of the patient;
    a preliminarily storing step of preliminarily storing geometrical display patterns representing profiles of the three spherical members, the axes connecting the center points of the three spherical members, and a profile of the auxiliary marker members including the linear portions;
    an image displaying step of forming a three-dimensional image utilizing CT image data acquired by imaging a patient who wears the medical imaging marker, and displaying the three-dimensional image and a desired sectional image of the three-dimensional image;
    a geometrical display pattern displaying step of reading the stored geometrical display patterns and displaying the geometrical display patterns in superposition with the sectional image displayed in the image displaying step;
    an image adjusting step of adjusting the displayed sectional image in response to input of an adjustment signal; and
    a coordinate system defining step of acquiring coordinates of the center points of the three spherical members in the adjusted sectional image and defining a reference coordinate system for the three-dimensional image utilizing the coordinates of the center points of the three spherical members.

7. A medical imaging marker utilization method recited in claim 6, wherein the base includes an external coordinate system provided on its surface and having a predetermined coordinate relationship with respect to an internal coordinate system defined by the center points of the three spherical members.

8. A medical imaging marker utilization method recited in claim 6, wherein the auxiliary marker members are planar members having two opposed parallel surfaces, and wherein each of the auxiliary marker members is disposed with the two surfaces thereof being parallel to a plane extending through the center points of the three spherical members.

9. A medical imaging marker as set forth in claim 3, wherein the base includes an external coordinate system provided on its surface and having a predetermined coordinate relationship with respect to an internal coordinate system defined by the center points of the three spherical members.

10. A medical imaging marker as set forth in claim 2, wherein the base includes an external coordinate system provided on its surface and having a predetermined coordinate relationship with respect to an internal coordinate system defined by the center points of the three spherical members.

11. A medical imaging marker utilization method recited in claim 9, wherein the auxiliary marker member includes polygonal or cylindrical columnar auxiliary marker members each having a predetermined length and being disposed so that the axes connecting the center points of the three spherical members respectively extend through centers of the auxiliary marker members.

12. A medical imaging marker as set forth in claim 1, wherein the base comprises a bottom base piece and a top base piece that is substantially vertically symmetrical with respect to the bottom base piece, the top base piece being inverted with respect to the bottom base piece.

13. A medical imaging marker as set forth in claim 1, wherein the rear portion of the base is substantially wider than the front portion of the base.

14. A medical imaging marker as set forth in claim 1, wherein the non-imageable material is an acryl resin.

15. A medical imaging marker utilization method as set forth in claim 6, wherein the non-imageable material is an acryl resin.

* * * * *